(12) United States Patent
Ahotupa (10) Patent No.: US 6,833,473 B1
(45) Date of Patent: Dec. 21, 2004

(54) KITS FOR QUANTIFYING OXIDATION PARAMETERS OF LOW DENSITY LIPOPROTEINS AND USES THEREOF

(75) Inventor: Markku Ahotupa, Turku (FI)

(73) Assignee: Oy Aboatech AB, Turku (FI)

( * ) Notice: Subject to any disclaimer, the term of this patent is extended or adjusted under 35 U.S.C. 154(b) by 0 days.

(21) Appl. No.: 09/270,480

(22) Filed: Mar. 15, 1999

(51) Int. Cl.$^7$ ............................................. C07C 51/31
(52) U.S. Cl. ..................................................... 562/543
(58) Field of Search ......................................... 562/543

(56) References Cited

U.S. PATENT DOCUMENTS 5,874,313 A * 2/1999 Ahotupa ...................... 436/71

FOREIGN PATENT DOCUMENTS

AT    94 01875    * 2/1999

OTHER PUBLICATIONS

Ziora T. Spectropholomatric Determanation of Oxidized LDL Klin biochem Metab 6(27)72 76, 1998.*
Winland H. A Simple Specific Method for Precipitation of LDL Lipid Research 24:904–909, 1983.*
Seccia M. Suitability of Chemical in vitro Models to Investigate LDL Oxidation. Clinical Chemistry 43(8)1436–1441, 1997.*
Vassankari T. Measment of Serum Lipid Peroxidation During Exercise Using Three Different Methods. Clinica Chimica Acta 234:63–69, 1995.*
Valkonen M. Spectrophotometric Assay for Total Peroxyl Radical Trapping Antioxidant Potential in Human Serum. J of Lipid Research 38(4)823–833, 1997.*

* cited by examiner

Primary Examiner—Ralph Gitomer
(74) Attorney, Agent, or Firm—Wolf, Greenfield & Sacks, P.C.

(57) ABSTRACT

Kits are provided for use in the screening of the risk for, the diagnosis, management and research of atherosclerosis and coronary heart disease comprising means for isolating LDL from a serum or plasma sample for the preparation of a LDL fraction, and means for separating the lipids from the LDL fraction to obtain a lipid fraction. The kit can further include a means for use in the determination of the level of conjugated dienes (LDL-BDC) in the lipid fraction. The invention also relates to a kit for in the above mentioned purpose including means for isolating LDL from a serum or plasma sample for the preparation of a LDL fraction, and means for use in the determination of the antioxidant potential of LDL in the sample. The invention further provides a kit for use in the above mentioned purpose including means for isolating LDL from a serum or plasma sample for the preparation of a LDL fraction, means for separating the lipids from the LDL fraction to obtain a lipid fraction, means for use determination of LDL-BDC in the lipid fraction, and means for use in the determination of the antioxidant potential of LDL in the sample. Additional kits and improved methods for analysis of LDL-BDC and/or LDL-TRAP are provided.

14 Claims, 8 Drawing Sheets

KITS FOR QUANTIFYING OXIDATION PARAMETERS OF LOW DENSITY LIPOPROTEINS AND USES THEREOF

FIELD OF THE INVENTION

The present invention relates to methods for measuring oxidation parameters of low density lipoproteins (LDL), which methods are rapid, simple to perform, and valid for the determination of LDL oxidation products and LDL antioxidant potential. These methods provide specific means for assessing the oxidative stress in the body of an individual in general and, in particular, for assessing or screening the risk for, and for the diagnosis, management and research of atherosclerosis and coronary heart disease.

BACKGROUND OF THE INVENTION

Oxidation of low-density lipoprotein plays a key role in processes leading to the development of atherosclerosis. LDL oxidation is accompanied by alterations in its biological properties resulting in, for example, accelerated uptake through scavenger receptors in macrophages, altered chemotactic behavior of monocytes, and monocyte-derived macrophages, endothelial cell damage, and increased amounts of mediators of cell proliferation and platelet aggregation (refs. 1–4). All these effects may contribute to the development of atherosclerotic lesions. Therefore, determination of the LDL oxidation related parameters, namely LDL oxidation products, and antioxidant potential, gives more specific information on atherosclerosis-related biochemical phenomena than the commonly used measurements, of which the most common are the measurement of serum cholesterol, LDL and other lipoproteins and the apolipoproteins.

Most of the data on LDL oxidation come from studies where oxidation of LDL fractions, isolated by conventional ultracentrifugation methods, has been monitored by the appearance of conjugated dienes or thiobarbituric acid reactants arising during oxidation of isolated LDL in vitro (5). Thus far, when LDL oxidation has been investigated in humans in vivo, analyses of LDL oxidation products have been based on antibodies raised against in vitro oxidatively damaged LDL (5). The existing methodology is complex and time-consuming and, in addition, the specificity of the immunological analyses can be questioned (3). Therefore, there is still need for single rapid and specific measurement of LDL oxidation that could become part of the laboratory repertoire in the diagnosis and management of atherosclerosis (5).

The immunological methods developed for direct measurement of oxidized LDL may not be specific, as, in addition to oxidized LDL, antibodies seem to recognize also other epitopes (6) and have given contradictory results as well (3). The poor applicability of immunological methods may be a reflection of the chemistry of LDL oxidation: LDL oxidation can be initiated in various different polyunsar fatty acids, and each of these can give rise to a number of different kinds of oxidation products. Due to the multiplicity of oxidation products, development and use of immunological methods is likely to remain problematic also in the future.

The existing methods for measuring the antioxidant potential of LDL are complex and time consuming, and for example only a limited number of analyses can be performed within one working week: LDL is first isolated by ultracentrifugation, whereafter the samples still have to be dialyzed. Another disadvantage is the unprecise recording of results, where changes of the various reaction phases are not always easily detected.

We have developed, for the analysis of LDL oxidation parameters, namely LDL oxidation products and LDL antioxidant potential, methods which are rapid and simple to perform, and can therefore be used for large-scale clinical studies. The validity and clinical applicability of these analytical procedures is clearly indicated by several studies.

SUMMARY OF THE INVENTION

The objects of the present invention are fulfilled by providing a kit for use in the screening of the risk for, the diagnosis, management and research of atherosclerosis and coronary heart disease comprising means for isolating LDL from a serum or plasma sample for the preparation of a LDL fraction, and means for separating the lipids from the LDL fraction to obtain a lipid fraction.

In a preferred embodiment of this invention, the means for isolating the LDL from the serum or plasma sample is a buffered heparin solution and the means for separating the lipids is a chloroform-methanol solution.

According to a further embodiment, the kit comprises a means for use in the determination of the baseline level of conjugated dienes (LDL-BDC) in the lipid fraction. Said means is preferably an organic solvent, and more preferable cyclohexane.

It is a further object of this invention to provide a kit for use in the screening of the risk for, the diagnosis, management and research of atherosclerosis and coronary heart disease comprising means for isolating LDL from a serum or plasma sample for the preparation of a LDL fraction, and means for use in the determination of the antioxidant potential of LDL (LDL-TRAP) in the sample.

According to a preferred embodiment, the means for isolating the LDL from the sample is a buffered heparin solution, the means for use in the determination of the antioxidant potential of LDL in a serum or plasma sample is 2,2'-azobis(2-amidinopropane)HCl (ABAP). The LDL-TRAP is preferably determined by using chemiluminescence.

It is still a further object of this invention to provide a kit for use in the screening of the risk for, the diagnosis, management and research of atherosclerosis and coronary heart disease comprising means for isolating LDL from a serum or plasma sample for the preparation of a LDL fraction, means for separating the lipids from the LDL fraction to obtain a lipid fraction, means for use in the determination of LDL-BDC in the lipid fraction, and means for use in the determination of the antioxidant potential of LDL (LDL-TRAP) in the sample.

Further areas of applicability of the present invention will be apparent from the detailed description given hereinafter.

The kits of the present invention can comprise a combination of the individual components needed to screen the risk for, diagnose, manage and research atherosclerosis and coronary heart disease presented together in a common pack. For this purpose, the kit can comprise separate vials or containers for the necessary reagents and substrates.

According to another aspect of the invention, improved kits and assay methods are provided. The kits are useful for quantifying oxidation parameters in a LDL fraction, optionally in a pre-isolated LDL fraction. The kits include in separate containers reagents for determining baseline levels of conjugated dienes, as described herein, in improved ratios and amounts. Other kits are usefull for quantifying antioxidant potential in a LDL fraction of blood serum or plasma, optionally in a pre-isolated LDL fraction. Such kits contain in separate containers unexpectedly improved and novel formulations, ratios and quantities of reagents for determining total peroxyl radical trapping antioxidant potential. The reagents include precipitants for precipitating an LDL fraction from blood or serum, solvents and solvent mixtures for extracting lipids from the LDL fraction, resuspension solvents and solvent mixtures for resuspending the LDL fractions and/or lipids isolated therefrom, and detection reagents for enabling or improving the detection of measurable assay end products. The improvements in methodology and equivalent instructions with the kits of the invention include sample handling, mixing and centrifugation parameters as are described herein.

Thus in some embodiments, kits for use in quantifying oxidation parameters of lipids in a LDL fraction of blood serum or plasma are provided. The kits include a first container for extracting the lipids from the LDL fraction, the first container containing a solvent which extracts lipids from a LDL fraction and a second container containing an amount of resuspension solvent sufficient to resuspend the extracted lipids. In certain embodiments, the solvent which extracts lipids is chloroform:methanol having a ratio greater than about 2:1, preferably greater than about 3:1, and more preferably about 4:1. In other embodiments, the resuspension solvent in the second container is neutral or inert to spectrophotometric analysis. Preferably the resuspension solvent in the second container is cyclohexane. Instructions for measuring absorbance at 234 nm and 300 nm, as well as calculation of LDL-BDC from the absorbance also can be included.

In still other embodiments, kits for use in determining antioxidant potential of a LDL fraction of blood serum or plasma are provided. The kits include a first container for extracting lipids from the LDL fraction, the first container containing a solvent which extracts lipids from a LDL fraction, and a second container containing an amount of a compound which produces peroxyl radicals sufficient to induces lipid peroxidation of the LDL fraction. Preferably the compound in the second container is 2,2'-azobis(2-amidinopropane)HCl (ABAP). In some embodiments, the ABAP is in a dry or solid form such as a powder and the kit includes a third container containing a solution for suspension of the ABAP. In other preferred embodiments, the kits include a third container containing a compound which enhances luminescence, which preferably is luminol. The kits also can include instructions for use of greater than about 25 $\mu$g of luminol per assay, more preferably greater than about 50 $\mu$g luminol per assay, even more preferably greater than about 75 $\mu$g per assay and most preferably about 88.5 $\mu$g per assay.

Kits for isolation of LDL from a blood or serum sample are provided in other embodiments. The kits include a container containing a buffered heparin solution, and instructions for adding a sufficient quantity of the buffered heparin solution to the blood or serum sample to form a LDL precipitate, mixing the mixture gently, and centrifuging the resulting mixture for at least 20 minutes to recover the LDL precipitate.

Kits combining two or more aspects of the foregoing kits also are provided, including kits for measuring LDL-BDC and LDL-TRAP, etc.

The method for determining LDL-BDC is based on the determination of the "diene conjugation," by which is meant the rearrangement of the double bonds in polyunsaturated fatty acids, which is an early event in the process of lipid peroxidation (7). This rearrangement is known to cause a specific change in UV-absorption of the fatty acid molecule. This is advantageous in two important ways: (i) diene conjugation occurs only during peroxidation of polyunsaturated fatty acids; (ii) diene conjugation is a common step in peroxidation of all polyunsaturated fatty acid molecules. In experimental in vitro studies on LDL oxidizability, the diene conjugation is regarded as the most reliable index, and is widely used in this context (5). The LDL-BDC method, however, is the first method used for the direct measurement of LDL diene conjugation in vivo without oxidation of the serum or plasma sample.

The method for measuring the antioxidant potential (LDL-TRAP) is, in contrast to the previously known methods, rapid (isolation of LDL and the measurements are done within the same day) and accurate.

BRIEF DESCRIPTION OF THE DRAWINGS

The invention as well as other objects, features and advantages thereof will be understood more clearly and fully from the following detailed description, with references to the accompanying drawings, in which:

FIG. 3 shows the linearity of A. LDL-BDC and B. LDL-TRAP with respect to sample size and reproducibility of the heparin-citrate precipitation method.

DETAILED DESCRIPTION OF THE INVENTION

According to a preferred embodiment of the present invention, LDL is isolated by a fast precipitation method and the assay for LDL oxidation products (LDL-BDC) is based on spectrophotometric determination of baseline levels of conjugated dienes (BDC) in lipids extracted from LDL. The assay kits also in certain embodiments are useful for measuring LDL-BDC and/or LDL-TRAP using LDL preparations made by other isolation methods, such as ultracentrifugation and immunological methods.

For performing the LDL-BDC and LDL-TRAP assays, 0.5 ml of serum or plasma is generally sufficient. In addition to fresh serum or plasma, frozen samples (studied for a period of 6 months at $-70°$ C.), too, can be used for the assays after thawing at room temperature.

According to a preferred embodiment of the invention, serum LDL is preferably isolated by precipitation with buffered heparin (8) after allowing the serum samples and precipitation reagents to equilibrate to room temperature. The serum sample, the volume of which can suitably be 0.2 to 1.7 ml, preferably 0.5 to 1 ml, is added to 1 to 7 ml, preferably 3.5 ml to 7 ml, of the precipitation buffer and mixed. It is preferable that the step of mixing be done gently, for example, avoiding the use of a vortex mixer. Initially the methods used vortex mixing as it was thought to provide gentle yet thorough mixing of the sample and heparin. Tests of mixing procedures indicated that gentle mixing provided improved results as compared to vortex mixing.

The insoluble lipoproteins are then sedimented by centrifugation and the pellet is resuspended in a sodium phosphate buffer, pH 7.4 to 8.0 (0.5 to 1 ml). As a result of extensive testing, it was determined that centrifugation is preferably carried out for greater than 10 minutes, and more preferably for at least 20 minutes. Unexpectedly, longer centrifugation times increased the assay-to-assay reliability by reducing the fluctuation of assay results. In the event that the LDL samples are not analyzed immediately after the preparation thereof, it is preferable to add EDTA to the buffer. The LDL sample or fraction thus obtained can be used as such for the quantification of oxidation products and antioxidant potential.

For measuring the LDL-BDC, lipids are extracted from LDL samples with a suitable organic solvent or solvent system, such as a chlorinated organic solvent, e.g. a chlorinated alkane, with a lower aliphatic alcohol. The sample size is usually 0.05 to 0.50 ml, preferably 0.10 ml. The chlorinated organic alkane can be e.g., chloroform or methylene chloride, although other chlorinated alkanes will be known to one of ordinary skill in the art. Similarly, the preferred lower aliphatic alcohol is methanol, but other lower aliphatic alcohols which are useful in the invention will be known to one of ordinary skill in the art. Preferably, the organic solvent is chloroform and the lower aliphatic alcohol is methanol. The chloroform:methanol ratio may range from 2:1 to 4:1, and is preferably 4:1 or 3:1. Testing of the assay with different proportions of these solvents indicated that a ratio of 4:1 chloroform:methanol was more preferable. The volume of the chlorinated alkane/lower aliphatic alcohol mixture added to the sample depends on sample size and ranges from 3 to 20 ml.

Water is added to the foregoing sample mixture, mixed by vortex mixing, and the resulting mixture is centrifuged to separate the phases. The lower phase is isolated and dried under an inert gas such as argon or nitrogen, preferably under nitrogen, then redissolved in an organic solvent, which is "inert" in the subsequent spectrophotometrical analysis. Examples of useful organic solvents include inert aliphatic hydrocarbons, e.g. alkanes or cycloalkanes, preferably a cyclohexane. The redissolved sample is analyzed spectrophotometrically at 234 and 300 nm, which provides an improved accuracy for the LDL-BDC assay by subtracting out the contribution of impurities or components other than conjugated dienes which absorb at 300 nm. The spectrophotometrical analysis is preferably performed in 10 minutes after the drying step.

The result is obtained by subtracting the absorbance at 300 nm from that at 234 nm. The $\Delta$ absorbance may be converted to molar units using the molar extinction coefficient $2.95 \times 10^4$ $M^{-1}cm^{-1}$. The results can be expressed in $\mu mol/l$ serum to give an estimation of the actual level of circulating oxidized LDL.

Significant and unexpected improvements in the foregoing LDL-BDC assay include the use of chloroform:methanol at 4:1, and the unexpected reduction of assay component volumes through optimization of the method steps. Previously the chloroform:methanol:water ratio used in the assay was 8:4:10. The presently configured method and kit provides for reduced consumption of reagents, which not only reduces cost per assay, but also reduces the amount of solvents used and disposed. The improved method and kit also provide improved accuracy and reproducibility because the same reaction tubes can be used throughout the entire assay, which was not previously possible.

The assay for the antioxidant potential (total peroxyl radical trapping antioxidant potential, TRAP) of LDL (LDL-TRAP) is based on a luminometric determination of the ability of LDL to resist peroxyl radical-induced lipid peroxidation. The sensitive chemiluminescence-based detection allows exact determination of the lag time period.

For such a measurement, sodium phosphate incubation buffer, pH 7.4, and the LDL sample (buffer 0.45 ml, sample size 0.05 to 0.20 ml, preferably 0.10 ml) are mixed in a cuvette and the assay is initiated by addition of a reagent which produces peroxyl radicals to create peroxyl radical-induced lipid peroxidation of LDL. The preferred reagent is 2,2'-azobis(2-amidinopropane)HCl (ABAP), but other reagents known to one of ordinary skill in the art which induce peroxyl radical-induced lipid peroxidation also can be used. The kits of the invention preferably include in a separate container an appropriate amount of ABAP in a dry form (e.g., powder), which form is more stable tan ABAP liquid. Thus, for the amounts indicated herein (e.g., 50 $\mu l$ of a 83 g/L solution of ABAP), a separate container containing about 4.15 mg and instructions for addition of an appropriate solvent (e.g. phosphate buffer) to prepare an ABAP solution are provided. Preferably the ABAP is solubilized immediately prior to use.

Chemiluminescence is measured at 37° C. until a peak value for each sample is detected. The method in one embodiment uses a combination of luminol and linoleic acid to enhance luminescence. It now has been discovered, quite unexpectedly, that linoleic acid can be omitted from the assay (thus avoiding the disadvantages resulting from its oxidation), and the quantity of luminol can be increased to obtain superior results. Thus in preferred embodiments, the method and kits of the invention do not use or contain linoleic acid, but instead use or contain luminol in an amount greater than 25 $\mu g$ per assay. More preferably the methods and kits use greater than 50 $\mu g$ luminol per assay, even more preferably greater than 75 $\mu g$ per assay and most preferably the amount of luminol used is about 88.5 $\mu g$ per assay. The improved luminescence reagents provide equivalent results in an assay that is simpler to perform (having one luminescence reagent rather than two), and yields improved assay-to-assay variability (less fluctuation of results).

Determination of the peroxyl radical trapping capacity is based on lag time determination which is defined by the half-peak time point, and trolox is used as a standard radical scavenger. To get an estimation of the relative antioxidant power of given LDL preparations, the results can be expressed in relation to the cholesterol concentration of the preparations.

Figure 1:
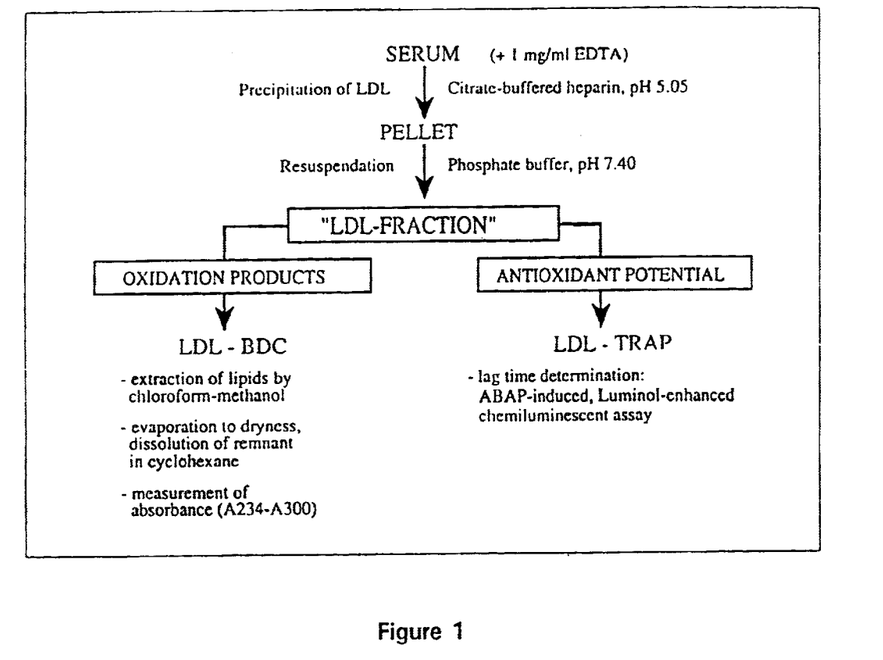
FIG. 1 is an overview of the preferred methods for determination of LDL oxidation products (LDL-BDC) and antioxidant potential (LDL-TRAP) in the serum.

An overview of the preferred measurements of LDL-BDC and LDL-TRAP is indicated in the FIG. 1.

According to the present invention it has been clearly indicated that:

BDC and TRAP can be readily measured in LDL by the described methods.

Measurement of LDL-BDC can be done in a similar way in heparin precipitated LDL as in LDL isolated by ultracentrifugation, the heparin precipitation method, however, offering several advantages over ultracentrifugation especially from a laboratory technical point of view.

The results obtained by the LDL-BDC method are well in accordance with those obtained by the immunological method.

High LDL-BDC values are indicative of increased risk for atherosclerosis, as suggested by the positive correlation with the thickness of arterial wall, and also indirectly by the results from studies where the LDL-BDC levels were found to alter parallelly to various known factors increasing the risk (diabetes, obesity etc.) for, or protecting (physically active life-style etc.) from atherosclerosis.

The LDL-TRAP value is indicative of the antioxidant potential of LDL, as indicated by the negative correlation with LDL-BDC, and also by the antioxidant intervention studies.

The results obtained in the LDL-BDC and LDL-TRAP methods can thus be used as indicators in the screening of the risk for, the diagnosis and management, including follow-up treatment, of atherosclerosis and coronary heart disease. In addition, these methods will be useful in a broad scale of studies and research on the etiology (e.g. the role of genetic, dietary, environmental or life style-dependent factors), prevention (e.g. the effect of dietary factors, physical activity, drugs) and management of atherosclerosis and coronary heart disease.

The reference ranges for LDL-BDC and LDL-TRAP are obtained laboratory specifically by measuring the LDL-BDC and LDL-TRAP values of a large number (e.g. 200–300) healthy human adults and calculating the corresponding mean values (with standard deviations). A high LDL-BDC value (close to the upper limit of the LDL-BDC reference range or over it), optionally in combination with a low LDL-TRAP value (close to the lower limit of the LDL-TRAP reference range or below it), is indicative of an increased risk for atherosclerosis and/or coronary heart disease. The reference ranges measured by us for healthy human individuals are LDL-BDC appr. 15–60 $\mu$mol/l serum and LDL-TRAP appr. 12–38 $\mu$mol/mmol LDL-cholesterol.

Due to the fact that the LDL-TRAP gives a faster response as a result of treatment and/or changes in life-style habits (diet, exercise), this value is especially advantageous for use as an easy and rapid means for the treatment follow-up of atherosclerosis and coronary heart disease.

The following Examples will further illustrate the present invention, which by no means limit the invention.

EXAMPLES

Example 1

Assays for LDL-BDC and LDL-TRAP
Precipitation of LDL

Serum LDL was isolated by precipitation with buffered heparin. The precipitation buffer was 0.064 M trisodium citrate adjusted to pH 5.05 with 5 N HCl, containing 50,000 IU/L heparin (5,000 IU/ml heparin was obtained either from Lövens Kemiska Fabrik, Ballerup, Denmark, or from Leiras Ltd, Turku, Finland). Before precipitation of LDL, serum samples (to which 1 mg/3.5 ml of EDTA is added) and precipitation reagents were allowed to equilibrate to room temperature.

One milliliter of the serum sample was added to 7 ml of the precipitation buffer. After mixing with a Vortex mixer, the suspension was allowed to stand for 10 min at room temperature. The insoluble lipoproteins were then sedimented by centrifugation at 1,000 g for 10 min. The pellet was resuspended in 1 ml of 0.1 M sodium phosphate buffer, pH 8.0, containing 0.9% of NaCl. This LDL sample was used as such for the analysis of oxidation products and antioxidant potential.

Determination of the Oxidation Products of LDL (LDL-BDC)

Lipids were extracted from LDL samples (sample size 0.10 ml) by adding 1 ml of methanol and 3 ml of chloroform (mixing with a Vortex mixer after the addition of each solvent). Then the mixture was allowed to stand for one hour at room temperature in the dark, after which 2 ml of water was added; the mixture was mixed with a Vortex mixer and then centrifuged at 2,000 g for 10 min at +8° C. The lower phase was evaporated to dryness under nitrogen, resuspended in 1 ml of cyclohexane and analyzed spectrophotometrically (Perkin-Elmer Lambda 2 spectrophotometer) at 234 and 300 nm.

Determination of the Antioxidant Potential of LSL (LDL-TRAP)

Figure 2:
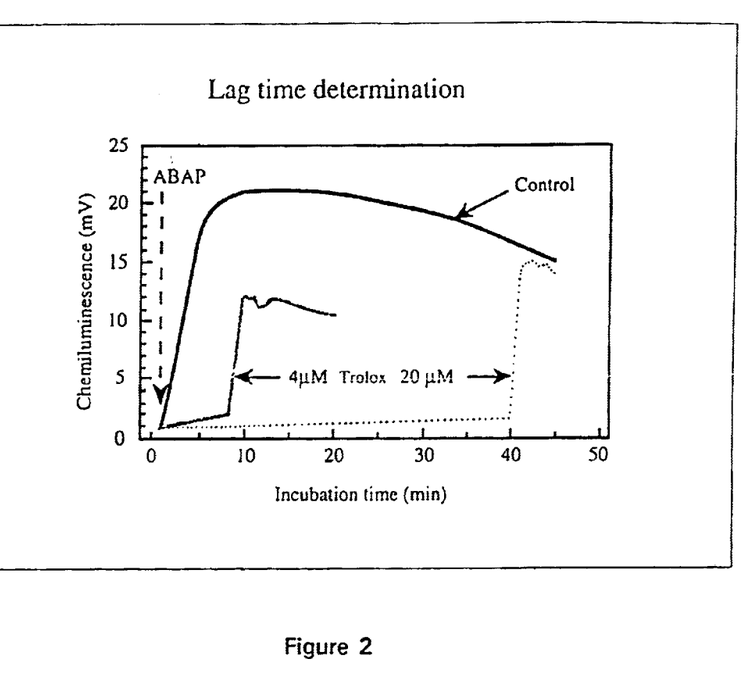
FIG. 2 is a graph, which shows the chemiluminescence lag time determination assay for LDL antioxidant potential (LDL-TRAP).

0.45 ml of incubation buffer (0.1M sodium phosphate buffer, pH 7.4, containing 0.9% of NaCl, 0.02 ml of 120 mM linoleic acid, 0.05 ml of luminol [0.5 mg/ml, obtained from Bio-Orbit Ltd., Turku, Finland]) and 0.10 ml of LDL sample were mixed in the cuvette and the assay was initiated with 0.05 ml of ABAP (83 mg/ml, obtained from Polysciences Inc., Warrington, Pa., USA). Chemiluminescence measurements were performed with Bio-Orbit 1251 Luminometer. Chemiluminescence in duplicate cuvettes was measured at 37° C. until a peak value for each sample was detected (see FIG. 2).

Validity of the Methods

Heparin precipitation is a specific and reproducible means for isolation of LDL from serum samples. In this LDL preparation, LDL-BDC and LDL-TRAP can be measured and the assays show good reproducibility and linearity, as can be seen from the results shown below.

To assess the reliability of the heparin-citrate precipitation method, the linearity with respect to sample size and reproducibility of the method were investigated. The reproducibility of LDL precipitation was tested by repeating the procedure 20 times from a pool of serum, and analyzing the apolipoprotein B (apoB) contents in precipitated LDL. Reagent kits for apolipoprotein B was obtained from Orion Diagnostica, Espoo, Finland. The coefficient of variation (CV) for the within-assay precision was 6.7% for apoB.

Figure 3:
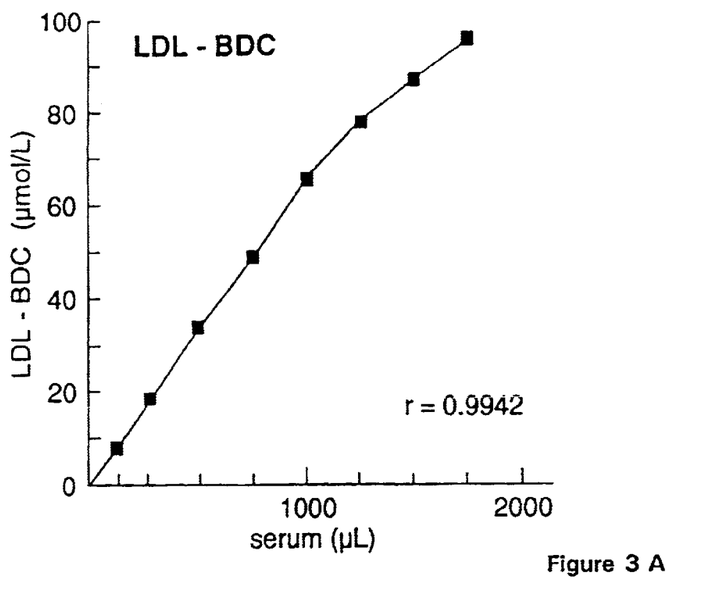

The LDL-BDC was detectable in LDL precipitated from 100 $\mu$l of serum, and the amount of LDL-BDC was directly proportional to the amount of serum taken for precipitation (FIG. 3A). Similarly, LDL-TRAP increased linearly with increasing amounts of serum and was reliably detectable in LDL precipitated from 260 $\mu$l of serum (FIG. 3B). For LDL-BDC, the CV for within-assay precision was 4.4%, and CV for the between-assay precision over a period of 3 months was 4.5%. With the LDL-TRAP, the CV for the within-assay precision was 8.1, and CV for the between-assay precision over a period of 3 months was 8.7%.

Freezing of the serum (studied for a period of 6 months at −70° C.) did not affect LDL-BDC or LDL-TRAP levels.

The relationship between LDL-BDC and LDL-TRAP and the corresponding measurements in serum, serum lipids, and antioxidants (α-tocopherol, ubiquinol-10), were measured in volunteers (n=31) and the interdependence of the parameters was estimated by correlation analysis. A reagent kit for cholesterol (CHOD-PAP method) was obtained from Boehringer Mannheim, Mannheim, Germany, and the serum concentrations of α-tocopherol (9) and ubiquinol-10 (10) were analyzed by standard HPLC procedures with UV-detection. There was a negative correlation between LDL-BDC and LDL-TRAP (Table 1). LDL-BDC correlated positively with serum diene conjugation, LDL cholesterol, and triglycerides, but no correlation was found to exist between the antioxidant levels and LDL-BDC. LDL-TRAP correlated positively with the serum TRAP value and negatively with serum LDL and cholesterol. Again, no correlation existed between the measured antioxidants and the LDL-TRAP.

The fact that the LDL-BDC and LDL-TRAP values are negatively correlated, further strengthens the validity and credibility of these methods. BDC values measured in heparin precipitated LDL are not different from those measured in LDL isolated by the conventional ultracentrifugation method, as shown by detailed comparison studies (Table 2). For preparative ultracentrifugation we used either a Sorvall OTD-65 ultracentrifuge with fixed-angle rotors or a Kontron TGA-65 ultracentrifuge with swing-out rotors (11, 12). The LDL-TRAP, however, was in this comparison lower in LDL isolated by precipitation. Since no dialysis was performed for LDL after ultracentrifugation, the apparently different TRAP values in LDL factions isolated by the different methods are likely explained by interfering peroxyl radical trapping components, such as ascorbate, glutathione and urate, present in LDL isolated by ultracentrifugation.

Of the direct methods currently available for estimation of LDL oxidation products, the preferred one has been the immunological method, based on the use of auto-antibodies to epitopes on oxidized LDL (5). When analyzed in the same samples from healthy volunteers (men, age 21–44 years, N=29), this immunological assay shows a good correlation with the LDL-BDC assay (FIG. 4).

Figure 4:
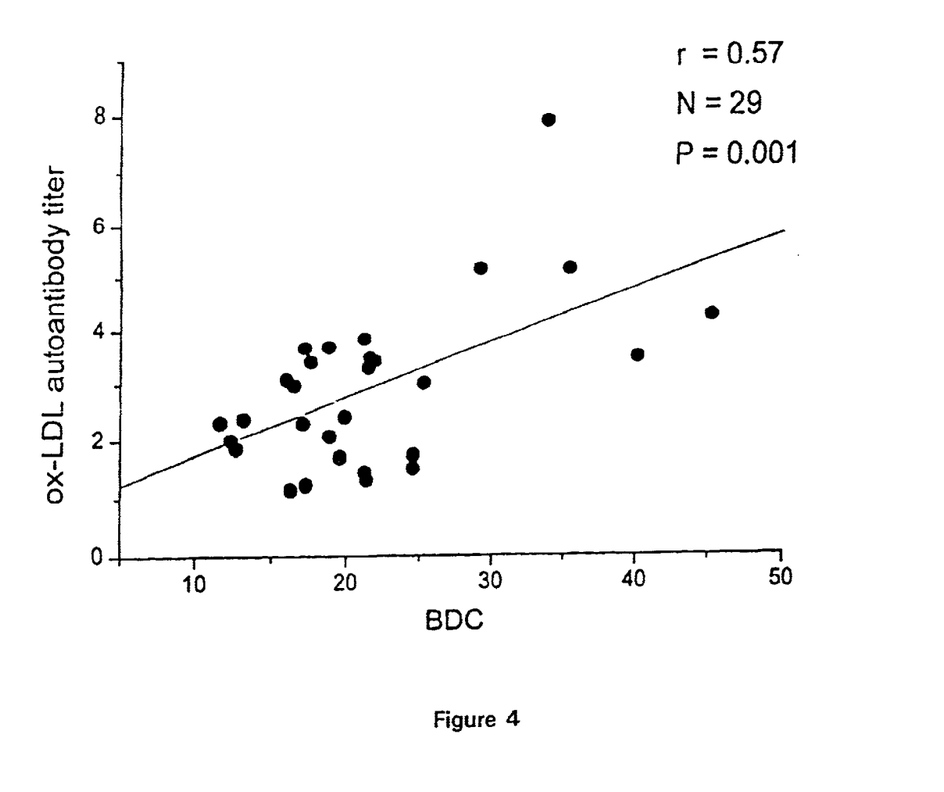
FIG. 4 is a graph which shows the correlation of LDL-BDC with oxidized LDL measured with the (conventional) immunological autoantibody method.

For obtaining the results in FIG. 4, autoantibody titers of anti-oxidized LDL were measured by enzyme-linked immunosorbent assay method using 96-well polystyrene microtitration plates (Nunc, Immunioplate, Roskilde, Denmark). Antigens for this assay included native LDL, protected against oxidation by 0.27 mM edetic acid and butylated hydroxytoluene (BHT) in phosphate buffered saline (PBS, 10 mM sodium phosphate, pH 7.2), and ox-LDL (obtained after 18 h oxidation with 2 μM $CuSO_4$, and prepared from the pooled plasma of ten donors (12). The wells were incubated (coated) with 50 μL of native and ox-LDL antigen (5 μg/ml) (protected from oxidation as noted above) in PBS for 16 h at 4° C. After removal of the unbound antigen and washing of the wells (three times with PBS, 0.5% Tween 20, and three times with distilled water, using microtiter plate washer BioRad Model 1550), the remaining non-specific binding sites were saturated using 2% bovine serum albumin in PBS. The wells were washed, and 50 μL of serum sample (diluted to 1:20 and 1:50) were added to wells coated with native LDL and ox-LDL, and incubated over night at 4° C. After incubation, the wells were aspirated and washed, before an appropriate IgG-peroxidase conjugated rabbit antihuman monoclonal antibody (Organon, USA, no, 55220 Cappel, diluted to 1:4,000 in 0.27 mM PBS, 20 μM edetic acid, 1 % BHT, bovine serum albumin-0.05% Tween) was added to each well (0.5 ml). After incubation (for 4 h at 4° C.), the unbound material from the wells were aspirated and wells washed. After this, 0.5 ml of freshly prepared substrate (0.4 mg/ml o-phenylenediamine, Sigma, and 0.045% $H_2O_2$ in 100 mM acetate buffer, pH 5.4) was added and incubated for 5 min at room temperature. The enzyme reaction was terminated by addition of 0.5 ml of 2M $H_2SO_4$. The optical density was then measured spectrophotometrically at 492 nm with a special microplate reader (Multiscan MCC/340, Labsystems GmbH, Munich, Germany). To calculate the antibody titer, we used the ratio of the corresponding spectrophotometric reading of anti-oxidized LDL and the anti-native LDL wells from the same serum sample. Using this approach, the spectrophotometric readings of anti-native LDL wells represent the corresponding blanks of anti-oxidized LDL wells and reduce the possible detection of false positive values.

TABLE 1

Correlation of LDL oxidation parameters with serum parameters related to LDL oxidation among healthy volunteers (N = 31).

|  | LDL-BDC | LDL-TRAP |
| --- | --- | --- |
| LDL-TRAP | −0.416[1] (p = 0.002) |  |
| Serum BDC | 0.647 (p = 0.0001) | −0.061 (p = 0.756) |
| Serum TRAP | 0.098 (p = 0.600) | 0.546 (p = 0.0015) |
| LDL | 0.676 (p = 0.0001) | −0.565 (p = 0.0009) |
| Serum cholesterol | 0.658 (p = 0.0001) | −0.467 (p = 0.0081) |
| Serum triglycerides | 0.732 (p = 0.0001) | −0.0002 (p = 0.999) |
| Serum α-tocopherol | 0.066 (p = 0.735) | 0.019 (p = 0.922) |
| Serum ubiquinol-10 | 0.357 (p = 0.057) | 0.074 (p = 0.701) |

[1]Correlation coefficient

TABLE 2

Baseline diene conjugation (BDC), thiobarbituric acid reactive material (TBARM) and antioxidant potential (TRAP) in serum and lipoprotein fractions isolated by sequential ultracentrifugation (UC) or heparin precipitation (HEP). Isolation of LDL by ultracentrifugation was performed by the standard procedure as described in ref. 18. LDL isolation by ultracentrifugation was performed by the standard procedure as described in ref. 18. LDL isolation by ultracentrifugation and heparin precipitation was repeated 4 times, on separate days and with freshly prepared serum pools. The Roman numerals indicate the different isolation times and serum pools. Results for the various isolation times/serum pools are given as μmol/l, and are mean ± SD from 6 different determinations (from each serum pool, 6 separate LDL samples were isolated). "Total mean" is the mean ± SD of means of the four different serum pools. VLDL, very low-density lipoprotein; HDL, high-density lipoprotein.

|  | Pool | BDC | TBARM | TRAP |
| --- | --- | --- | --- | --- |
| SERUM | I | 71.8 ± 2.7 | 7.40 ± 1.41 | 1071 ± 0 |
|  | II | 68.1 ± 1.1 | 6.60 ± 0.85 | 1193 ± 34 |
|  | III | 57.7 ± 5.9 | 8.20 ± 0.28 | 1071 ± 69 |
|  | IV | 68.3 ± 1.4 |  | 803 ± 34 |
|  | Total mean | 66.5 ± 6.1 | 7.40 ± 0.80 | 1035 ± 165 |
| UC-VLDL | I | 26.4 ± 6.4 | 0.14 ± 0.003 | 206 ± 17 |
|  | II | 20.9 ± 3.3 | 0.20 ± 0.26 | 149 ± 17 |
|  | III | 16.3 ± 2.4 | 0.17 ± 0.12 | 244 ± 35 |
|  | IV | 18.0 ± 3.2 |  | 131 ± 26 |
|  | Total mean | 20.4 ± 4.4 | 0.17 ± 0.12 | 244 ± 35 |
| UC-LDL | I | 25.1 ± 2.8 | 0.43 ± 0.10 | 229 ± 17 |
|  | II | 26.3 ± 2.9 | 0.07 | 200 ± 13 |
|  | III | 23.4 ± 1.1 | 0.18 ± 0.11 | 191 ± 18 |
|  | IV | 30.8 ± 1.8 |  | 192 ± 27 |

TABLE 2-continued

Baseline diene conjugation (BDC), thiobarbituric acid reactive material (TBARM) and antioxidant potential (TRAP) in serum and lipoprotein fractions isolated by sequential ultracentrifugation (UC) or heparin precipitation (HEP). Isolation of LDL by ultracentrifugation was performed by the standard procedure as described in ref. 18. LDL isolation by ultracentrifugation was performed by the standard procedure as described in ref. 18. LDL isolation by ultracentrifugation and heparin precipitation was repeated 4 times, on separate days and with freshly prepared serum pools. The Roman numerals indicate the different isolation times and serum pools. Results for the various isolation times/serum pools are given as $\mu$mol/l, and are mean ± SD from 6 different determinations (from each serum pool, 6 separate LDL samples were isolated). "Total mean" is the mean ± SD of means of the four different serum pools. VLDL, very low-density lipoprotein; HDL, high-density lipoprotein.

|  | Pool | BDC | TBARM | TRAP |
|---|---|---|---|---|
| UC-HDL | Total mean | 26.4 ± 3.2 | 0.23 ± 0.18 | 203 ± 18 |
|  | I | 12.6 ± 1.9 | 1.90 ± 0.21 | 288 ± 20 |
|  | II | 20.3 ± 2.3 | 1.27 ± 0.05 | 315 ± 13 |
|  | III | 15.3 ± 2.2 | 1.30 ± 0.14 | 261 ± 26 |
|  | IV | 19.0 ± 1.5 |  | 219 ± 16 |
|  | Total mean | 16.8 ± 3.5 | 1.49 ± 0.36 | 271 ± 41 |
| HEP-LDL | I | 25.1 ± 0.9 | 0.60 ± 0 | 46 ± 3 |
|  | II | 33.3 ± 13.6 | 0.15 ± 0 | 51 ± 3 |
|  | III | 24.6 ± 0.5 | 0.10 ± 0 | 49 ± 0 |
|  | IV | 26.7 ± 1.4 |  | 29 ± 0 |
|  | Total mean | 27.4 ± 4.0 | 0.28 ± 0.28 | 44 ± 10 |

Clinical Applicability of the Methods

Clinical applicability of LDL-BDC and LDL-TRAP has bee tested among patients and volunteers with known disease- or life style dependent factors increasing or decreasing the risk of atherosclerosis and coronary heart disease (CHD). In addition, applicability of the LDL-TRAP method has been tested by antioxidant intervention studies.

Progression of atherosclerosis is commonly estimated by measuring the thickness of the arterial walls by ultrasound techniques. The ultrasound technique was used for measurement of the (intima-media) thickness of arteria carotis among 33 men (age 21–46 years), and LDL oxidation products from these subjects were determined by the LDL-BDC method. A positive correlation (r=0.43; p=0.012) was found to exist between the LDL-BDC values and thickness of the arteria carotis.

Diabetes

Non-insulin-dependent diabetes is known to be associated with increased risk for atherosclerosis (13). Samples were collected from patients at the Department of Internal Medicine, Turku University Hospital, Finland. The material includes patients from both sexes, ages 16–88 years. No separation was made with respect to the type of diabetes mellitus and, at times of the sample collection, patients were receiving treatment for the disease.

Figure 5:
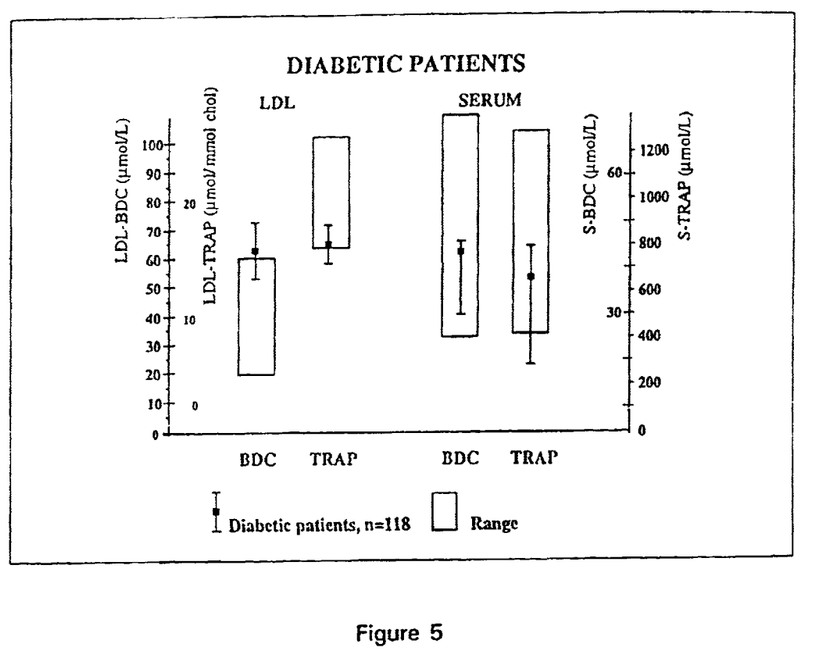
FIG. 5 shows the ranges of BDC and TRAP values of LDL and serum of diabetic patients. The term "range" means normal values based on determinations on healthy volunteers, age 18–70 years, both sexes, N=300.

FIG. 5 shows that LDL-BDC and LDL-TRAP values of patients with diabetes (N=118) clearly differ from those of age-matched healthy controls.

Obesity

Figure 6:
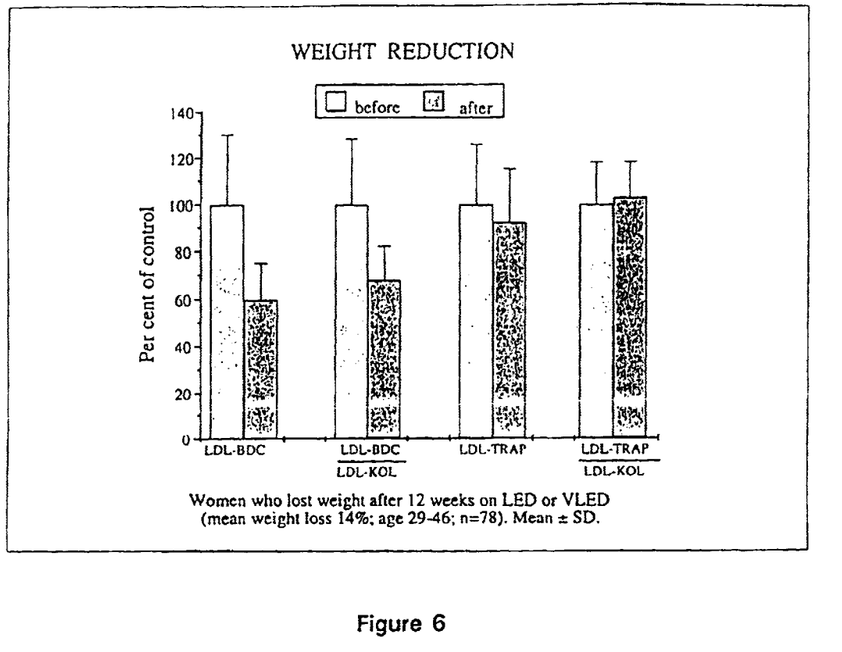
FIG. 6 is a bar graph, which shows the effect of body weight reduction on LDL-BDC and LDL-TRAP values in obese premenopausal women. Weight before onset of diets ranged from 90 to 100 kg. LED, low-energy diet; VLED, very low-energy diet.

Obesity is an independent risk factor for CHD mortality among men and also contributes to the risk of CHD among women (14). When measured in healthy volunteers (men, age 40–49 years, N=31) LDL-BDC was found to correlate positively with the body mass index (r=0.47, p=0.008). Controlled reduction of body weight among obese premenopausal women N=82, weight before onset of diets ranged from 90 to 100 kg) decreased significantly LDL-BDC levels. Total LDL-BDC decreased by 40% and LDL-BDC/total LDL cholesterol ratio by 32% (FIG. 6).

Physical Activity

Figure 7:
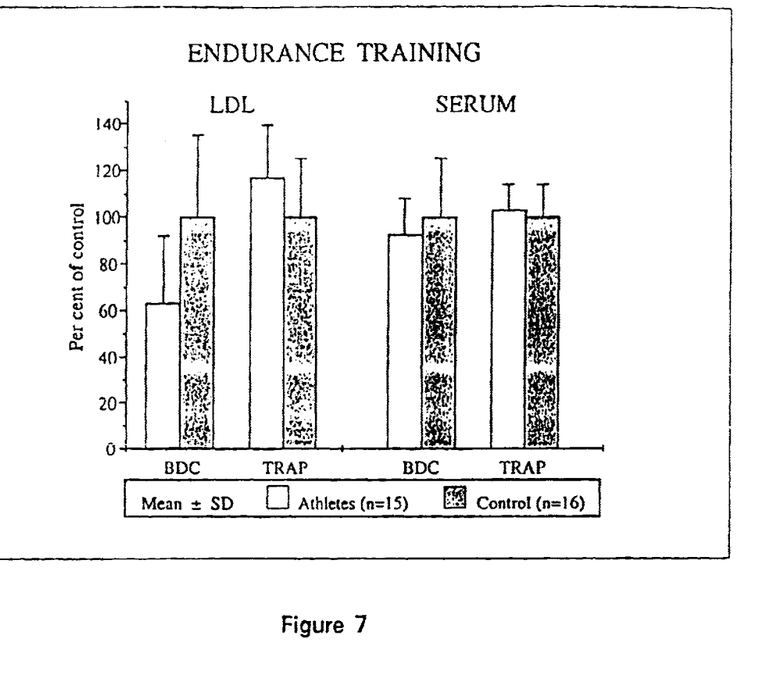
FIG. 7 is a bar graph, which shows the effect of endurance training on BDC and TRAP values in LDL and serum. "Athletes" denote a group of men (age 40–49 years) with a history of several (>15) years active endurance training (long-distance running). Control group consisted of men of the same age and weight (body mass index) with no endurance training, but a similar socioeconomic background and dietary and smoking habits.

Physically active life style, in turn, is known to be associated with decreased risk of CHD (15). We found that middle-aged (40–49 years) men (N=31) who are actively participating in endurance training have distinctly lower LDL-BDC values (37%) than age- and weight-matched controls with similar socioeconomic background, and dietary and smoking habits (FIG. 7, see also ref. 16).

Antioxidant Intervention

Figure 8:
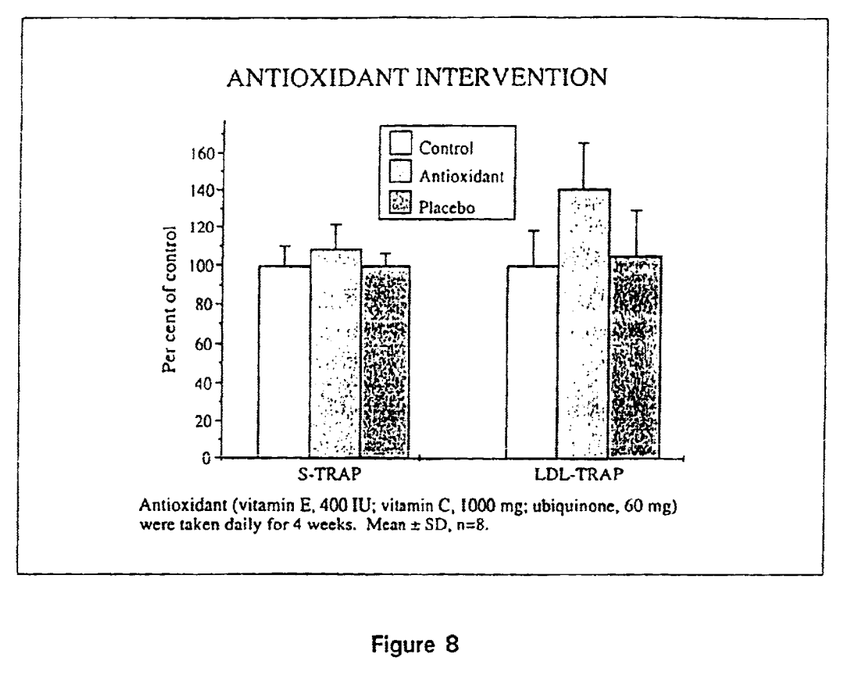
FIG. 8 is a bar graph, which shows the effect of antioxidant intervention on LDL-TRAP and serum TRAP (S-TRAP) values in endurance athletes. Men, age 26–39 years, with 6–21 years history of endurance training. The antioxidant preparations were as follows: vitamin E, Tokovitan®, d-α-tocopheryl acet., Orion, Espoo, Finland; vitamin C, Accorbin®, ascorbic acid, Orion, Espoo, Finland; ubiquinone, Coenzyme Q10®, ubidecarenon., RP Scherer Ltd, Wiltshire, UK Antioxidants were taken daily for 4 weeks (vitamin E:400 IU; vitamin C: 1000 mg; ubiquinone: 60 mg).

Two intervention studies have been performed to test the effect of antioxidant preparations (dietary supplements) on LDL-BDC and LDL-TRAP. In the first study (11) vitamin E alone or in combination with vitamin C and $\beta$-carotene was given to volunteers (N=10) a period of one week In the second (double blind) study (FIG. 8) volunteers received a combination of antioxidants (vitamin E, vitamin C and ubiquinone) for 4 weeks. Serum concentrations of $\alpha$-tocopherol and ubiquinol-10 were analyzed by standard HPLC procedures with UV-detection. In both of these studies LDL-TRAP values were found to be increased by the antioxidant interventions (by about 40%) while the LDL-BDC levels remained unaffected (for further details, see ref 17).

Example 2

Improved Assays for LDL-BDC and LDL-TRAP

Precipitation of LDL

Serum LDL was isolated by precipitation with buffered heparin The precipitation buffer is 0.064 M trisodium citrate-2-hydrate adjusted to pH 5.0 by 0.064 M citric acid, containing 50,000 Iu/L heparin and 286 mg/L of EDTA. Before precipitation of LDL, serum samples and precipitation reagents were allowed to equilibrate to room temperature.

To the serum sample (0.5 ml), 3.5 ml of the precipitation buffer was added. After gentle mixing, the suspension was allowed to stand for 10 min at room temperature. The insoluble lipoproteins were then sedimented by centrifugation at 970 g for 20 min at +8° C., after which the supernatant was discarded. The pellet was resuspended in 0.5 ml of 0.1 M sodium phosphate buffer, pH 8.0, containing 0.9% of NaCl and 286 mg/ml of EDTA. This LDL sample was used as such for the analysis of oxidation products and antioxidant potential. LDL isolated by other methods (e.g., ultracertrifugation) also is used as follows.

Determination of the Oxidation Products of LDL (LDL-BDC)

Lipids were extracted from LDL samples (sample size 0.10 ml) by adding 1 ml of methanol and 4 ml of chloroform. The mixture was mixed with a Vortex mixer and allowed to stand for 10 min at room temperature after the addition of each solvent. Thereafter, 2 ml of water was added, the mixture was properly mixed with a Vortex mixer and then centrifuged in a swinging bucket centrifuge (allowing up to 90° angle between the rotor axis and the tubes) at 1,500 g for 10 min at +8° C. The upper phase was discarded, and the lower phase was evaporated to dryness under nitrogen, then resuspended in 1 ml of cyclohexane and analyzed spectrophotometrically (Peridn-Elmer Lambda 2 spectrophotometer) at 234 and 300 nm, within 10 minutes.

Determination of the Antioxidant Potential of LDL (LDL-TRAP)

0.45 ml of incubation buffer (0.1M sodium phosphate buffer, pH 7.4, containing 0.9% of NaCl), 0.05 ml of luminol (1.77 mg/ml in 0.1M sodium borate, pH 9) [obtained from Bio-Orbit Ltd., Turku, Finland]) and 0.10 ml of LDL sample were mixed in a cuvette by vortex mixing. The assay was initiated with the addition of 0.05 ml of ABAP (83 mg/ml in 0.1M sodium phosphate buffer, pH 7.4, containing 0.9% of NaCl, obtained from Polysciences Inc., Warrington, Pa., USA). Chemiluminescence measurements were performed with Bio-Orbit 1251 Luminometer. Chemiluminescence in duplicate cuvettes was measured at 37° C. until a peak value for each sample was detected (see FIG. 2). Controls reactions were preformed by using in place of the LDL sample 0.1 ml of 0.1M sodium phosphate buffer, pH 8.0, containing 0.9% of NaCl and 286 mg/ml EDTA (reagent control), or 0.1 ml of 10 $\mu$mol/L trolox (6hydroxy-2,5,7,8-tetramethylchroman-2-carboxylic acid) in 0.1M sodium phosphate buffer, pH 8.0, containing 0.9% of NaCl and 286 mg/ml EDTA (standard). Results were calculated by the following equation:

$$20\times(\text{sample}-\text{reagent control}):(\text{standard}-\text{reagent control})\mu\text{mol/L}.$$

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. All documents referenced herein are incorporated by reference in their entirety.

I claim:

1. A kit for use in the screening of the risk for, the diagnosis, management and research of atherosclerosis and coronary heart disease comprising
    a container containing a reagent for isolating LDL from a serum or plasma sample for the preparation of a LDL fraction, and
    a container containing a reagent for use if the determination of the antioxodant potential of LDL (LDL-TRAP) in the LDL fraction.

2. The kit according to claim 1, wherein the reagent for isolating the LDL from the sample is a buffered heparin solution.

3. The kit according to claim 1, wherein the reagent for use in the determination of the antioxodant potential of LDL in a serum or plasma is 2.2'-azobis(2-amidinopropane)HCl (ABAP).

4. The kit for use in the screening of the risk for, the diagnosis management and research of atherosclerosis and coronary heart disease comprising
    a container containing a reagent for isolating LDL from a serum or plasma sample for the preparation of a LDL fraction,
    a container containing a reagent for separating the lipids from the LDL fraction to obtain a lipid fraction,
    a container containing a reagent for use in the determination of LDL-BDC in the lipid fraction, and
    a container containing a reagent for use in the determination of LDL-TRAP in the LDL fraction.

5. The kit according to claim 4, wherein the reagent for isolating the LDL from the serum or plasma is a buffered heparin solution.

6. The kit according to claim 4, wherein the reagent for separating the lipid is a chloroform-methanol solution.

7. The kit according to claim 4, wherein the reagent for use in the determination of LDL-BDC in the lipid fraction is an organic solvent.

8. The kit according to claim 7, wherein the reagent for use in the determination of LDL-BDC in the lipid fraction is a cyclohexane.

9. The kit according to claim 4, wherein the reagent for use in the determination of the antioxidant potential of LDL is the sample is 2.2'-azobis(2-amidinopropane)HCl (ABAP).

10. A kit for use in determining antioxidant potential of a LDL fraction of blood serum or plasma, comprising
    a first container for extracting lipids from the LDL fraction, first container containing a solvent which extracts lipids from a LDL fraction; and
    a second container containing an amount of a compound which produced peroxyl radicals sufficient to induces lipid peroxidation of the LDL fraction.

11. The kit according to claim 10, wherein the compound in the second container is 2.2'-azobis(2-amidinopropane) HCl (ABAP).

12. The kit of claim 11, wherein ABAP is a powder and further comprising a third container containing a solution for suspension of the ABAP.

13. The kit of claim 11, further comprising a third container containing a compound which enhances luminescence.

14. The kit of claim 13, wherein the compound which enhances luminescence is luminol.

* * * * *

UNITED STATES PATENT AND TRADEMARK OFFICE
CERTIFICATE OF CORRECTION

PATENT NO. : 6,833,473 B1
DATED : December 21, 2004
INVENTOR(S) : Markku Ahotupa It is certified that error appears in the above-identified patent and that said Letters Patent is hereby corrected as shown below:

Column 13,
Line 33, delete "if" and replace with -- in --;
Lines 34 and 40, delete "antioxodant" and replace with -- antioxidant --;
Line 41, after "plasma", insert -- sample --;
Line 41, delete "2.2" and replace with -- 2,2' --;
Line 43, delete "The" and replace with -- A --;

Column 14,
Line 12, after "plasma" insert -- sample --;
Line 23, delete "2.2'" and replace with -- 2,2' --;
Line 27, after "fraction," insert -- the --;
Line 30, delete "produced" and replace with -- produces --;
Line 34, delete "2.2'" and replace with -- 2,2' --;
Line 36, after "wherein" insert -- the --;

Signed and Sealed this

Twenty-second Day of March, 2005

JON W. DUDAS
*Director of the United States Patent and Trademark Office*